(12) United States Patent
Fortener

(10) Patent No.: US 10,874,166 B2
(45) Date of Patent: Dec. 29, 2020

(54) ADJUSTABLE CORRECTIVE SHOE COMPONENT

(71) Applicant: Susan Fortener, Alpharetta, GA (US)

(72) Inventor: Susan Fortener, Alpharetta, GA (US)

( * ) Notice: Subject to any disclaimer, the term of this patent is extended or adjusted under 35 U.S.C. 154(b) by 103 days.

(21) Appl. No.: 16/104,417

(22) Filed: Aug. 17, 2018

(65) Prior Publication Data

US 2019/0053570 A1 Feb. 21, 2019

Related U.S. Application Data

(60) Provisional application No. 62/547,654, filed on Aug. 18, 2017.

(51) Int. Cl.
| | | |
|---|---|---|
| *A43B 7/14* | (2006.01) | |
| *A43B 7/24* | (2006.01) | |
| *A61F 5/14* | (2006.01) | |
| *A43B 19/00* | (2006.01) | |
| *A43B 7/22* | (2006.01) | |
| *A43B 7/18* | (2006.01) | |
| *A61F 5/01* | (2006.01) | |

(52) U.S. Cl.
CPC ............... *A43B 7/24* (2013.01); *A43B 7/141* (2013.01); *A43B 7/142* (2013.01); *A43B 7/144* (2013.01); *A43B 7/1495* (2013.01); *A43B 7/18* (2013.01); *A43B 7/223* (2013.01); *A43B 19/00* (2013.01); *A61F 5/0111* (2013.01); *A61F 5/14* (2013.01)

(58) Field of Classification Search
CPC ........... A43B 7/14; A43B 7/141; A43B 7/142; A43B 7/1485; A43B 7/144; A43B 17/00; A43B 13/38; A43B 3/12; A43B 3/122; A43B 3/126

USPC ..... 36/88, 91, 140, 145, 166, 169, 170, 173, 36/11.5
See application file for complete search history.

(56) References Cited

U.S. PATENT DOCUMENTS

| | | | | | |
|---|---|---|---|---|---|
| 1,572,213 | A | * | 2/1926 | Wilbert ................ | A43B 3/0052 36/170 |
| 1,976,819 | A | * | 10/1934 | Weiler ................. | A43B 7/1495 36/166 |
| 2,038,151 | A | * | 4/1936 | Wernmark ............ | A43B 3/128 36/11.5 |
| 2,116,445 | A | * | 5/1938 | Moore .................... | A43B 7/00 36/170 |
| 2,126,094 | A | * | 8/1938 | Daniels ................. | A43B 3/122 36/11.5 |
| 2,149,664 | A | * | 3/1939 | Brown ................. | A43B 7/1495 36/170 |

(Continued)

*Primary Examiner* — Marie D Bays
(74) *Attorney, Agent, or Firm* — Rothwell, Figg, Ernst & Manbeck, P.C.

(57) ABSTRACT

An adjustable corrective shoe component is provided. The shoe component can be disposed in an inner lining of a shoe. The shoe component may include a shell formed conformal to an interior bottom surface of the shoe and curving upwards at sides of the shoe. The shell may include a forefoot section to accommodate a forefoot area of a foot, a middle section to accommodate a midfoot area of the foot, and a hind section to accommodate a hind area of the foot. The shoe component may include a strap attached to a medial side of the middle section and configured to pull the middle section towards a lateral side of the shoe to cause the middle section to support an arch of the foot.

15 Claims, 14 Drawing Sheets

(56) References Cited

U.S. PATENT DOCUMENTS

| | | | | |
|---|---|---|---|---|
| 2,182,843 | A | * | 12/1939 | Flynn .................... A43B 7/1495 36/170 |
| 2,404,083 | A | * | 7/1946 | Murray .................... A43B 7/00 36/140 |
| 2,642,677 | A | * | 6/1953 | Yates ...................... A43B 3/126 36/11.5 |
| 2,734,285 | A | * | 2/1956 | Levitt ...................... A43B 7/26 36/140 |
| 3,739,501 | A | * | 6/1973 | Barrett, Jr. .............. A43B 3/128 36/11.5 |
| 4,107,857 | A | * | 8/1978 | Devlin ..................... A43B 5/06 36/11.5 |
| 4,236,328 | A | * | 12/1980 | Friedlander .......... A43B 7/1495 36/117.5 |
| 4,300,294 | A | * | 11/1981 | Riecken ................... A43B 7/26 36/101 |
| 4,446,633 | A | * | 5/1984 | Scheinhaus ............ A43B 3/126 36/11.5 |
| 4,510,699 | A | * | 4/1985 | Nakamura ................ A61F 5/14 36/173 |
| 4,679,334 | A | * | 7/1987 | McBride ............ A43C 11/1493 36/11.5 |
| 4,794,706 | A | * | 1/1989 | Puckhaber ............... A43B 3/26 36/91 |
| 4,811,500 | A | * | 3/1989 | Maccano ................. A43B 5/00 36/117.9 |
| 4,813,162 | A | * | 3/1989 | Harris .................... A43B 3/108 36/11.5 |
| 5,323,549 | A | * | 6/1994 | Segel .................... A43B 7/1495 36/140 |
| 5,713,143 | A | * | 2/1998 | Kendall ................... A43B 7/14 36/145 |
| 5,960,566 | A | * | 10/1999 | Brown ..................... A43B 7/14 36/140 |
| 5,992,057 | A | * | 11/1999 | Monti ..................... A43B 5/02 36/50.1 |
| 6,021,585 | A | * | 2/2000 | Cole ...................... A43B 3/122 36/11.5 |
| 6,151,804 | A | * | 11/2000 | Hieblinger ............... A43B 5/02 36/128 |
| 6,173,511 | B1 | * | 1/2001 | Perrault ................. A43B 7/141 36/140 |
| 6,393,733 | B1 | * | 5/2002 | London ................ A43B 7/1495 36/155 |
| 6,393,736 | B1 | * | 5/2002 | Greer, Jr. .................. A61F 5/14 36/145 |
| 6,606,803 | B1 | * | 8/2003 | Ritter ..................... A43B 3/126 36/11.5 |
| 7,343,701 | B2 | * | 3/2008 | Pare ........................ A43C 1/06 36/50.1 |
| 7,788,827 | B2 | * | 9/2010 | Fogg ..................... A43B 13/026 36/59 C |
| D790,827 | S | * | 7/2017 | Fadil ............................. D2/961 |
| 2002/0148142 | A1 | * | 10/2002 | Oorei ...................... A43C 1/00 36/129 |
| 2005/0240139 | A1 | * | 10/2005 | Bushby .................. A43B 7/142 602/61 |
| 2006/0059712 | A1 | * | 3/2006 | Asham ................ A41B 11/121 36/11.5 |
| 2006/0059720 | A1 | * | 3/2006 | Phelan .................... A43B 3/242 36/101 |
| 2006/0236564 | A1 | * | 10/2006 | Allard ....................... A61F 5/14 36/140 |
| 2007/0283597 | A1 | * | 12/2007 | Logan ................... A61F 5/0111 36/91 |
| 2009/0090027 | A1 | * | 4/2009 | Baudouin ............ A43B 7/1495 36/93 |
| 2009/0133289 | A1 | * | 5/2009 | Cantoni ................. A43B 3/126 36/101 |
| 2011/0061262 | A1 | * | 3/2011 | Krauss ................... A61F 5/019 36/11.5 |
| 2012/0124860 | A1 | * | 5/2012 | Waddel ................. A43B 3/128 36/11.5 |
| 2013/0255105 | A1 | * | 10/2013 | Bishop ................... A43B 3/126 36/88 |
| 2014/0101969 | A1 | * | 4/2014 | Pham ..................... A43B 3/126 36/11.5 |
| 2014/0101975 | A1 | * | 4/2014 | Ueda .................... A43B 7/1495 36/131 |
| 2015/0082660 | A1 | * | 3/2015 | Ofray, Sr. ............ A41B 11/007 36/11.5 |
| 2018/0110285 | A1 | * | 4/2018 | Cohen .................... A43B 7/16 |

\* cited by examiner

ADJUSTABLE CORRECTIVE SHOE COMPONENT

CROSS-REFERENCE TO RELATED APPLICATIONS

This patent application claims benefit of U.S. Provisional application No. 62/547,654 filed Aug. 18, 2017. The subject matter of the aforementioned application is incorporated herein by reference for all purposes.

TECHNICAL FIELD

This disclosure generally relates to field of corrective shoes and more particularly to adjustable corrective shoe components.

BACKGROUND

The approaches described in this section could be pursued but are not necessarily approaches that have been previously conceived or pursued. Therefore, unless otherwise indicated herein, the approaches described in this section are not prior art to the claims in this application and are not admitted to be prior art by inclusion in this section.

Pronation and supination are natural movements of a foot when the foot absorbs and reflects ground forces. A challenge may develop when there are specific excessive deviations in the amount of these natural movements in the foot. There is no a perfect presentation for the foot. Every human has a pattern of movement defined by genetics, body development, or developmental disabilities. The human body accommodates for these deviations but often not without challenges to human gait. The challenges may cause pain, imbalance, or soft tissue disturbances in the foot structure and up in a kinetic chain. People are often unaware that their feet are still developing until the age of 14-16 years and that correction of feet can be influenced by many factors. Therefore, there is great neglect in the management of human feet from the early years of human growth which can grow into permanent developmental challenges.

Solution to correction of the foot is often an arduous scenario of steps to provide necessary treatment for foot correction. These steps are further complicated by high costs of treatment and health provider requirements for approving the treatment. Today, many people do not obtain treatment due to high costs, are treated over aggressively, or neglect accommodation due to the discomfort of current available remedies.

To get treatment, the individual or his caregiver faces a two-step process. The first step is an evaluation by a medical professional where often a custom device is ordered that implements corrections to the foot by adding lifts, wedges, or plastic that is placed to the underside of or around the foot. The second step is buying shoes into which the customer devices will be inserted. Such treatment is costly and time consuming due to the requirement for follow ups and modifications over wear time.

Medical coverage is changing. Insurance, Medicare, and Medicaid programs are greatly reduced as deductibles rise. Thus, there is a need for a device that may be purchased substantially off the shelf and require minimal customization, and yet is adjustable accommodation for necessary foot correction and protection for individuals in routine life activities, sport activities, and gait disabilities in every age group.

SUMMARY

This section is provided to introduce a selection of concepts in a simplified form that are further described below in the Detailed Description section. This summary is not intended to identify key features or essential features of the claimed subject matter, nor is it intended to be used as an aid in determining the scope of the claimed subject matter.

According to some embodiments of the disclosure, an adjustable corrective shoe component is provided. The adjustable corrective shoe component can be disposed in an inner lining of a shoe. The adjustable corrective shoe component may include a shell formed conformal to an interior bottom surface of the shoe and curving upwards at sides of the shoe. The shell may include a forefoot section to accommodate a forefoot area of a foot. The shell may include a middle section to accommodate a midfoot area of the foot. The shell may include a hind section to accommodate a hind area of the foot. The adjustable corrective shoe component may further include a strap attached to a medial side of the middle section of the shell. The strap can be configured to pull the middle section towards a lateral side of the shoe to cause the middle section to support an arch of the foot.

The shell can be made of a flexible material or a semifirm material. The strap can be made of a stretch material. The strap can be configured to be pulled through an eyelet, a loop, or a d-ring attached to the lateral side of the shoe and then pulled back and secured using a hook-and-loop fastener integrated in the strap.

The middle section of the shell can be separated from the hind section by a notch extending from a medial edge of the shell transversally to the center of the shell.

The adjustable corrective shoe component may further include a further strap attached to a medial side of the forefoot section. The further strap can be configured to pull the forefoot section towards the lateral side of the shoe to cause the forefoot section to support a metatarsal head or a toe. The further strap can be configured to be pulled over a surface of the shoe, through an eyelet, a loop, or a d-ring attached to the lateral side of the shoe, and then pulled back and secured using a hook-and-loop fastener integrated in the further strap.

The hind section of the shell may include a "U" cut from a back side of the foot. The adjustable corrective shoe component may further include a first back strap attached to a medial side of the hind section. The first back strap can be configured to be pulled through a surface of a shoe and towards a lateral external side of the shoe, and so cause the medial side of the hind section to support a medial side of a heel of the foot. The adjustable corrective shoe component may further include a second back strap attached to a lateral side of the hind section. The second back strap may be configured to be pulled through a surface of a shoe and towards a medial external side of the shoe, and so cause the lateral side of the hind section to support a lateral side of the heel of the foot. The first back strap and the second back strap can be crisscrossed within the shoe.

The adjustable corrective shoe component may further include a first hook-and-loop fastener to secure the first back strap to the lateral external side of the shoe. The adjustable corrective shoe component may further include a second hook-and-loop fastener to secure the second back strap to the medial external side of the shoe.

Additional objects, advantages, and novel features of the examples will be set forth in part in the description which follows, and in part will become apparent to those skilled in the art upon examination of the following description and the accompanying drawings or may be learned by production or operation of the examples. The objects and advantages of the concepts may be realized and attained by means of the methodologies, instrumentalities and combinations particularly pointed out in the appended claims.

BRIEF DESCRIPTION OF THE DRAWINGS

Embodiments are illustrated by way of example and not limitation in the figures of the accompanying drawings, in which like references indicate similar elements and in which.

Figure 11:
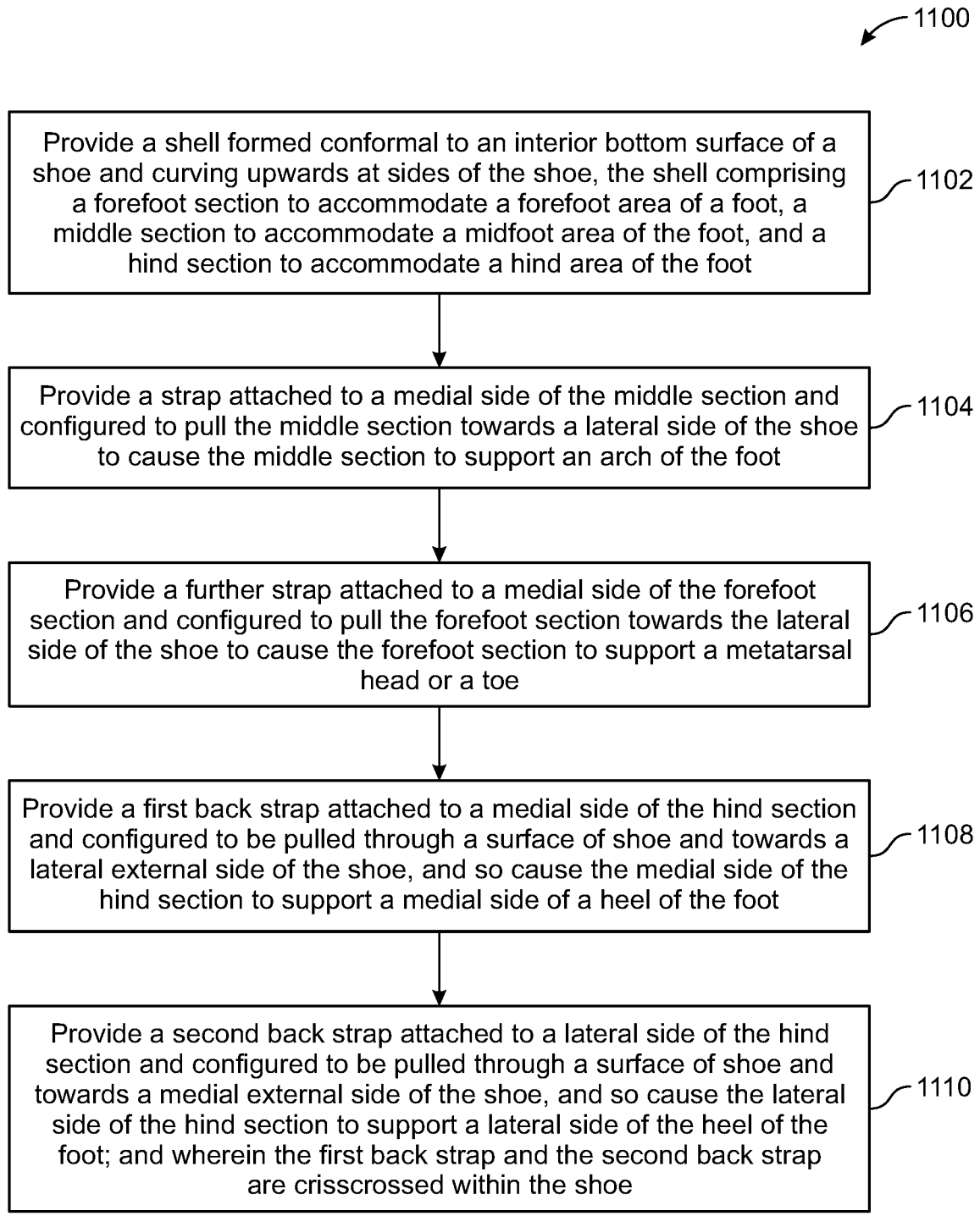

The FIG. 11 is a flow chart showing a method for manufacturing an adjustable corrective show component, according to an example embodiment.

DETAILED DESCRIPTION

The following detailed description of embodiments includes references to the accompanying drawings, which form a part of the detailed description. Approaches described in this section are not prior art to the claims and are not admitted to be prior art by inclusion in this section. The drawings show illustrations in accordance with example embodiments. These example embodiments, which are also referred to herein as "examples," are described in enough detail to enable those skilled in the art to practice the present subject matter. The embodiments can be combined, other embodiments can be utilized, or structural, logical and operational changes can be made without departing from the scope of what is claimed. The following detailed description is, therefore, not to be taken in a limiting sense, and the scope is defined by the appended claims and their equivalents.

Generally, the embodiments of this disclosure are concerned with adjustable corrective shoe inserts or components. Some embodiments of the present disclosure may provide adjustable corrective shoe components to be disposed within shoes.

An example adjustable corrective shoe component may include a corrective restraint type shell with track cutting, anchors, reliefs, and directional pull supports. The shell may include three parts for support of a foot. The first part is a toe medial or lateral adjustable toe strap. The second part is a sliding adjustable stretch strap to support the medial or lateral side of the foot. The third part is a tracked stirrup type strap that protects heel movement. The shell may be secured in the inner lining of a shoe to eliminate migration and shearing movement of the foot in the shoe. The shell may be made of a compressive, flexible, or semi firm type material that offers dynamic movement in each section of the foot. The shell may include a moderately firm dynamic skeletal shoe structure that allows unlimited adjustability to the medial and lateral forefoot and medial longitudinal arch, and posterior medial and lateral calcaneal wall support with an excavated heel to biomechanically control heel eversion and inversion.

The adjustable corrective shoe component may include a fore foot adjusting pull strap attached to the shell. The pull strap may include a stretch material. The pull strap may be attached anywhere along the underside midsection, lateral, or medial side of the structure at the fore foot and can be stitched, glued, or otherwise secured. The pull strap forms a pull system that may be pulled over the top of the foot over or under the shoe tongue in the direction of the outside of the foot wall over the outside of the shoe into a loop, d-ring, or strap eyelet integrated into the shoe and pulled back to attach on the upper part of the strap with a securing yet adjustable type of material such as hook and loop.

The adjustable corrective shoe component may further include a mid-section adjustable pull strap. The mid-section adjustable pull strap may be made of a stretch material and may be attached anywhere along the underside midsection, lateral, or medial side of the shell at the midfoot and can be stitched, glued, or accessory secured. The mid-section adjustable pull strap forms a pull system that may pulled over the top of the foot over or under the shoe tongue in the direction of the outside of the foot wall over the outside of the shoe into a loop, d-ring, or integrated strap eyelet into the shoe and is pulled back to attach on the upper part of the strap with a securing yet adjustable type of material such as hook and loop.

The shell may include various notches along the outer walls (medial, lateral, posterior). The shell may include a firm medial wall. The shell may include a "Sustentaculum Tali" break that supports the adjustability of the medial arch and gives the ability to accommodate the amount of support needed per individual, which may eliminate the need for an elevated intrinsic/extrinsic arch post. The shell may allow for multiple configurations and options on the outer shoe wall for total foot manipulation to accommodate various foot deviations.

The shell may include a "U" cutout in a hind section to accommodate a heel. The inner wall of the shell may include a posterior medial and lateral Achilles pillow to support a heel clasp. The adjustable shoe component may include straps attached to the shell above the "U" cutout. The straps may be pulled out of the back or side counter of the shoe and secured by pulling the strap on the outside of the medial and lateral side of the shoe counter with a hook and loop type material or pulled out and secured with a cord stop type accessory.

The shell may further include a lightweight, flexible, vertebrae sole. The sole may work in conjunction with pull straps attached to the wall of the shell to adjust the desired direction needed in fore-foot deviation in any foot structure. Thus, the shell and the straps attached to the wall of the shell may provide a three part adjustable control to the foot structure: fore-foot, midfoot, and hind-foot.

The adjustable corrective shoe component may be manufactured in volume and offered at economical prices so that an individual may purchase the adjustable corrective shoe component without having to be concerned with insurance coverage and costs. The individual may not need to visit a professional for custom adjustments of the adjustable corrective shoe component, as adjustments can be accommodated at home to provide stabilization during an individual's changing gait needs.

The embodiments of present disclosure are described with reference to the drawings. The drawings are schematic illustrations of idealized example embodiments. As such, variations from the shapes of the illustrations as a result, for example, of manufacturing techniques or tolerances, are to be expected. Thus, example embodiments discussed herein should not be construed as limited to the particular shapes of regions illustrated herein but are to include deviations in shapes that result, for example, from manufacturing or learned "best practices."

Figure 1:
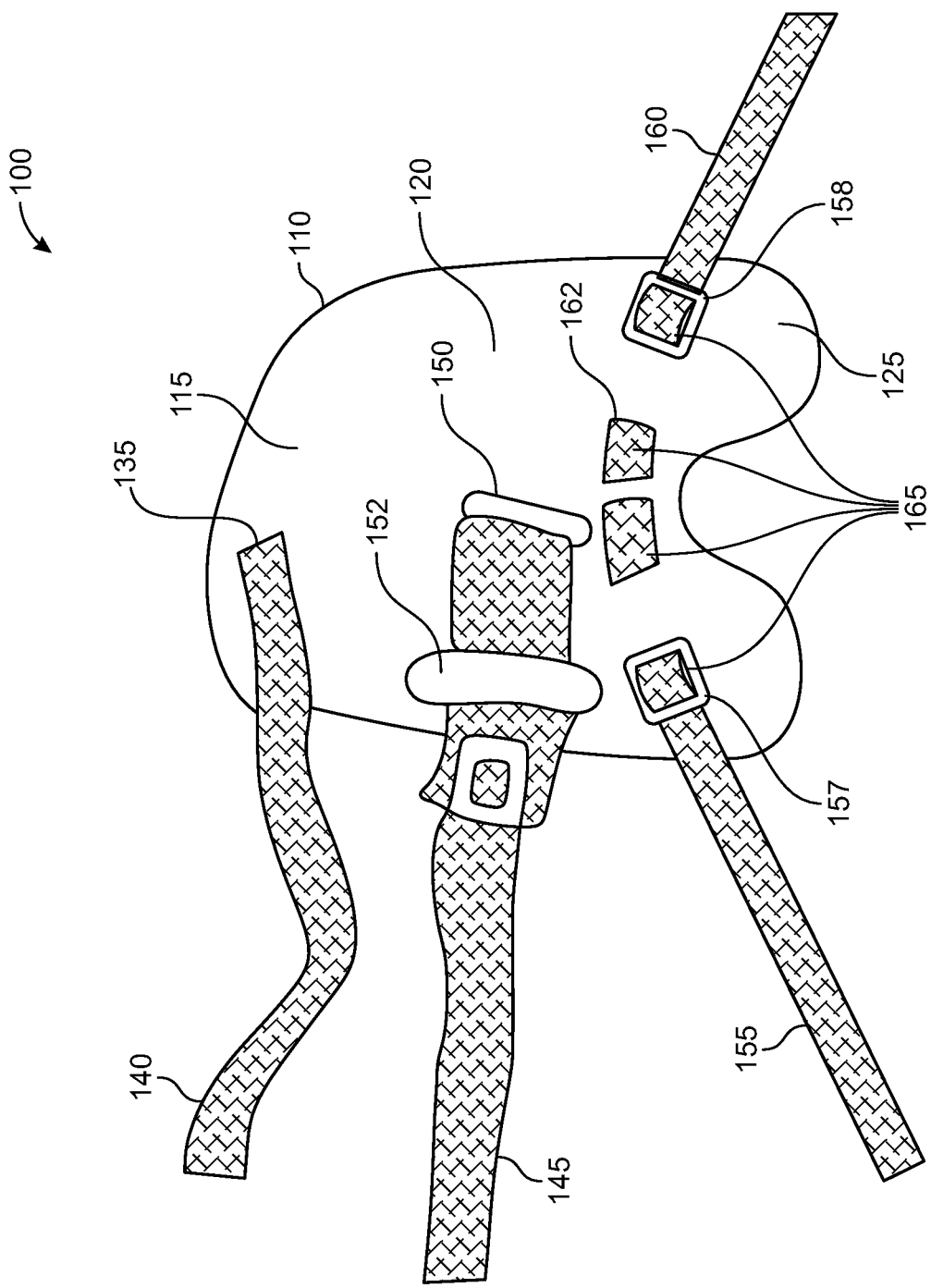
FIG. 1 shows a bottom surface of an adjustable corrective shoe component, according to an example embodiment.

FIG. 1 shows a bottom surface of an adjustable corrective shoe component 100, according to an example embodiment. The adjustable corrective shoe component 100 can be attached inside a left shoe. The adjustable corrective shoe component 100 may include a shell 110. The shell 110 may be made of flexible or semi-rigid material. The shell 110 can be disposed in an inner lining of a shoe. The shell 110 can be formed conformal to an interior bottom surface of the shoe and curving upwards at sides of the shoe. The shell 110 may include a forefoot section 115 to accommodate a forefoot area of a foot. The shell 110 may include a middle section 120 to accommodate a midfoot area of the foot. The shell 110 may include a hind section 125 to accommodate a hind area of the foot. The hind section 125 may include a "U" shaped cutout from the back side of the foot.

The adjustable corrective shoe component 100 may further include one or more straps attached to the bottom surface of the shell 110. A toe strap 140 can be attached to the bottom surface of the shell 110 using an anchor 135 within forefoot section 115. A navicular strap 145 can be attached to the bottom surface of the shell 110 using anchors 150 and 152 within the middle section from a medial side.

A first heel strap 155 can be attached to the bottom surface of the shell 110 using anchor 157 within the hind section 125 from a medial side. A second heel strap 160 can be attached to the bottom surface of the shell 110 using anchor 158 within the hind section 125 from a lateral side. A calcaneal stirrup 162 can be attached to the shell via tracking cuts 165 and using anchors 157 and 158.

The toe strap 140, the navicular strap 145, a first heel strap 155, and a second heel strap 160 may include an elastic stretch type material.

Figure 2:
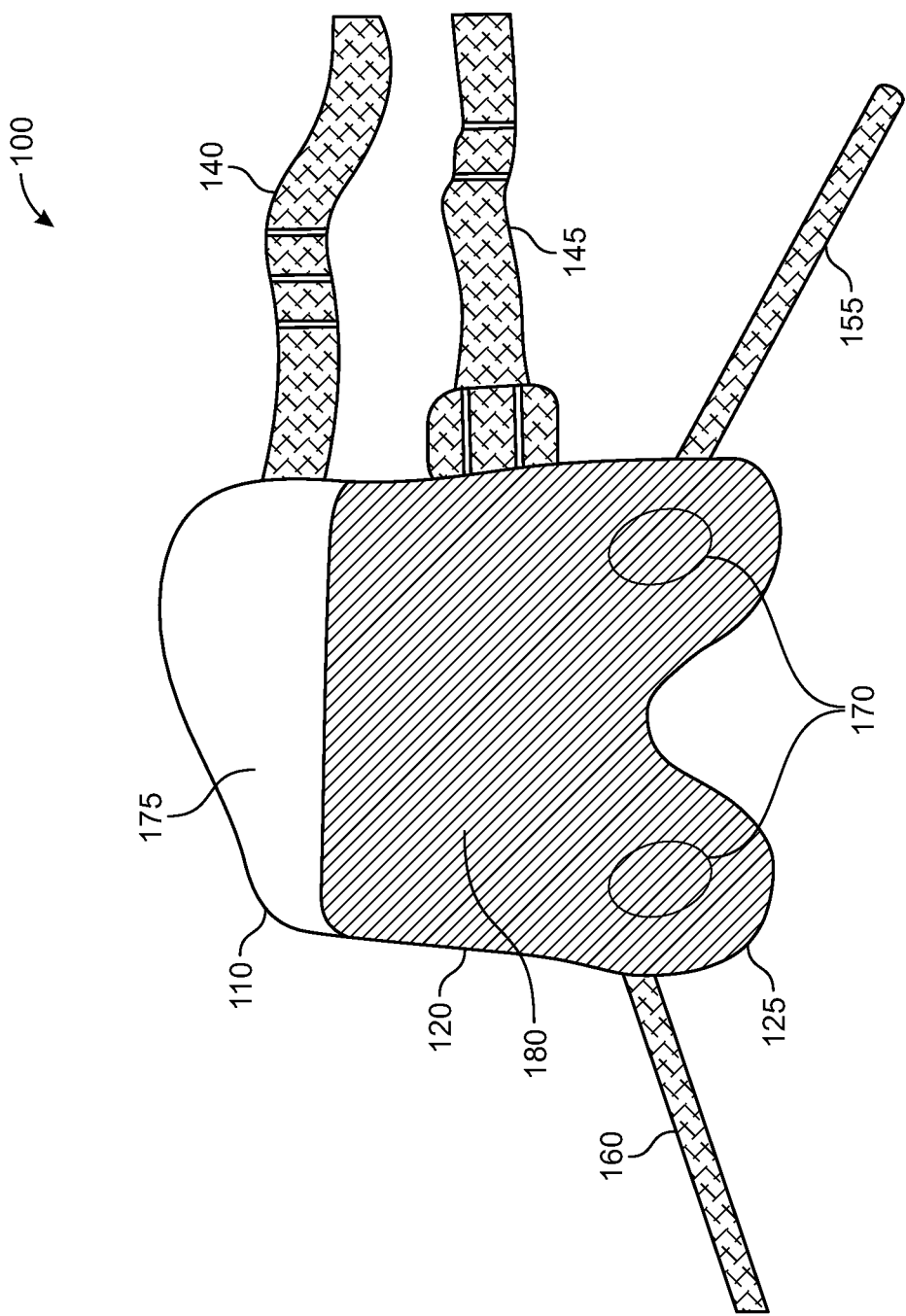
FIG. 2 shows a top surface of the adjustable shoe component of FIG. 1.

FIG. 2 shows a top surface of the adjustable shoe component 100. The shell 110 may include a first layer 175 and a second layer 180. The first layer 175 can be made of conformable material. The second layer 185 can be made of flexible ethylene-vinyl acetate (EVA) material or a cork type material. The shell 110 may include a "U" shaped cutout. The area of the "U" shaped cutout can be open so that the bottom of the heel of the individual's foot comes through the opening due to the "U" shaped cutout and comes in contact with the shoe. The hind section of the shell 110 may include two Achilles pillows 170 on the medial side and lateral side of the shell 110. The Achilles pillows 170 can be made of a soft foam or EVA material. The Achilles pillows 170 may provide an additional clasp for the heel such that the shell 110 comforts the heel and provides sensory support.

The toe strap 140 can be attached at a medial side of the forefoot section of the shell 110. The navicular strap 145 can be attached at a medial side of the middle section of the shell 110. The first heel strap 155 can be attached at medial side of the hind section of the shell 110. The second heel strap 160 can be attached at a lateral side of the hind section of the shell 110.

Figure 3:
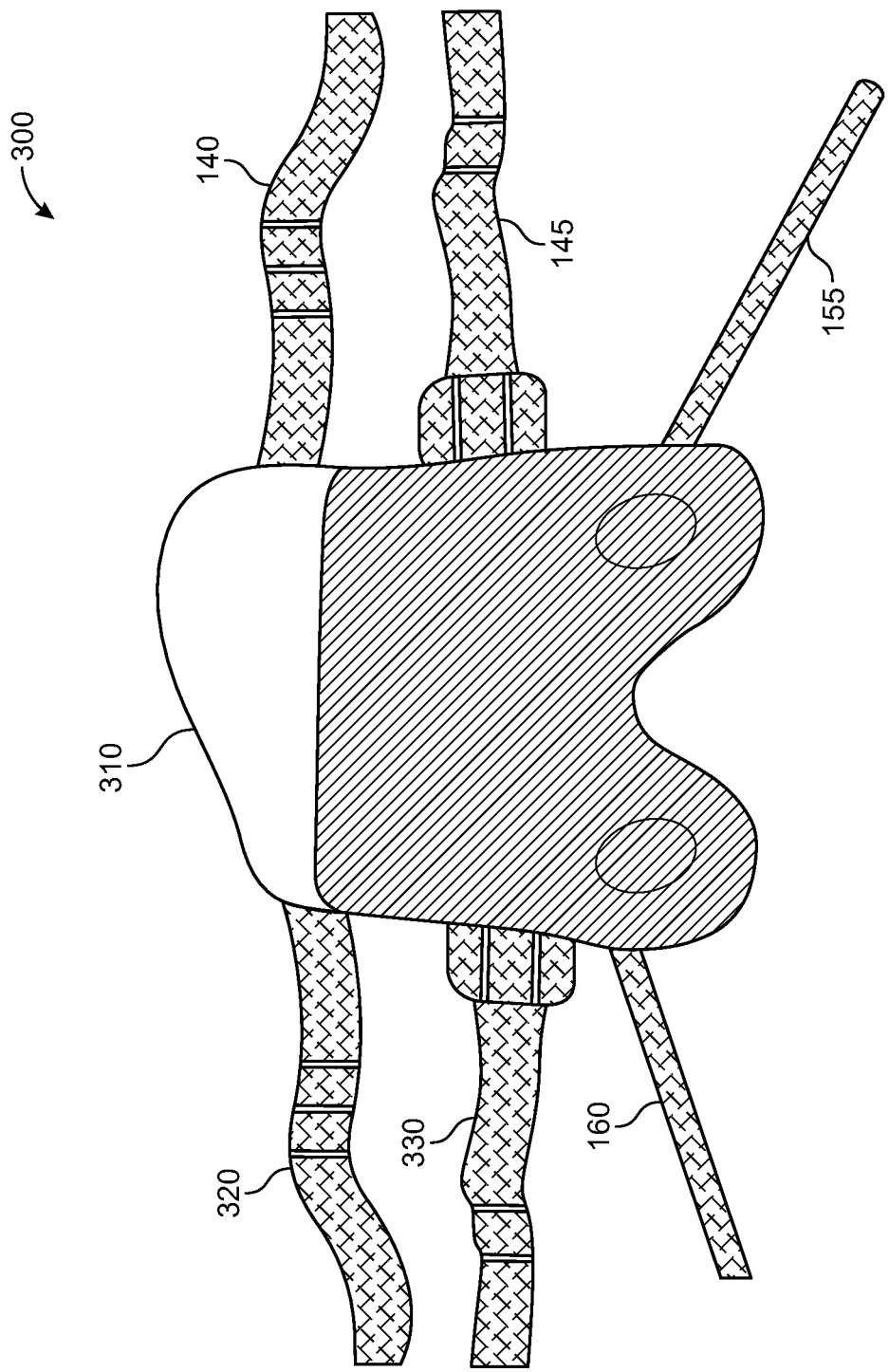
FIG. 3 shows a top surface of an adjustable corrective shoe component, according to another example embodiment.

FIG. 3 shows an upper surface of an adjustable corrective shoe component 300, according to another example embodiment. Similar to the adjustive corrective shoe component 100, the adjustive corrective shoe component 300 may include shell 310, a toe strap 140 attached at bottom of a medial side of forefoot section of the shell 300, a navicular strap 145 attached at bottom of a medial side of the middle section of the shell 310, a first heel strap 155 attached at medial side of the hind section of the shell 310, and a second heel strap 160 attached at lateral side of the hind section of the shell 310. Additionally, the adjustive corrective shoe component 300 may include a second toe strap 320 attached at bottom of a lateral side of forefoot section of the shell 310 and a second navicular strap 330 attached at bottom of a lateral side of the middle section of the shell 310.

Figure 4:
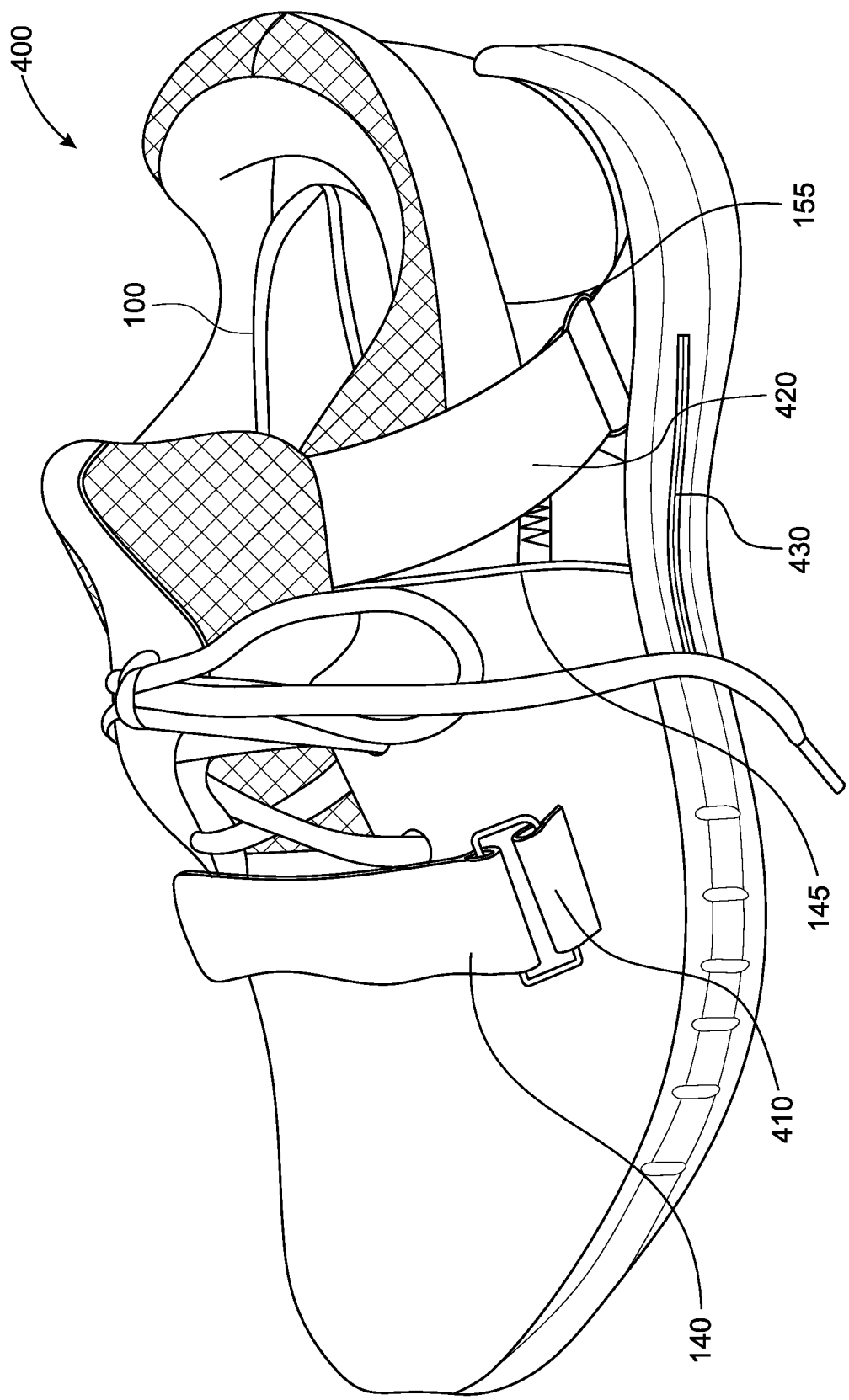
FIG. 4 is a lateral elevated view of a left shoe with an adjustable corrective shoe component, according to an example embodiment.
Figure 5:
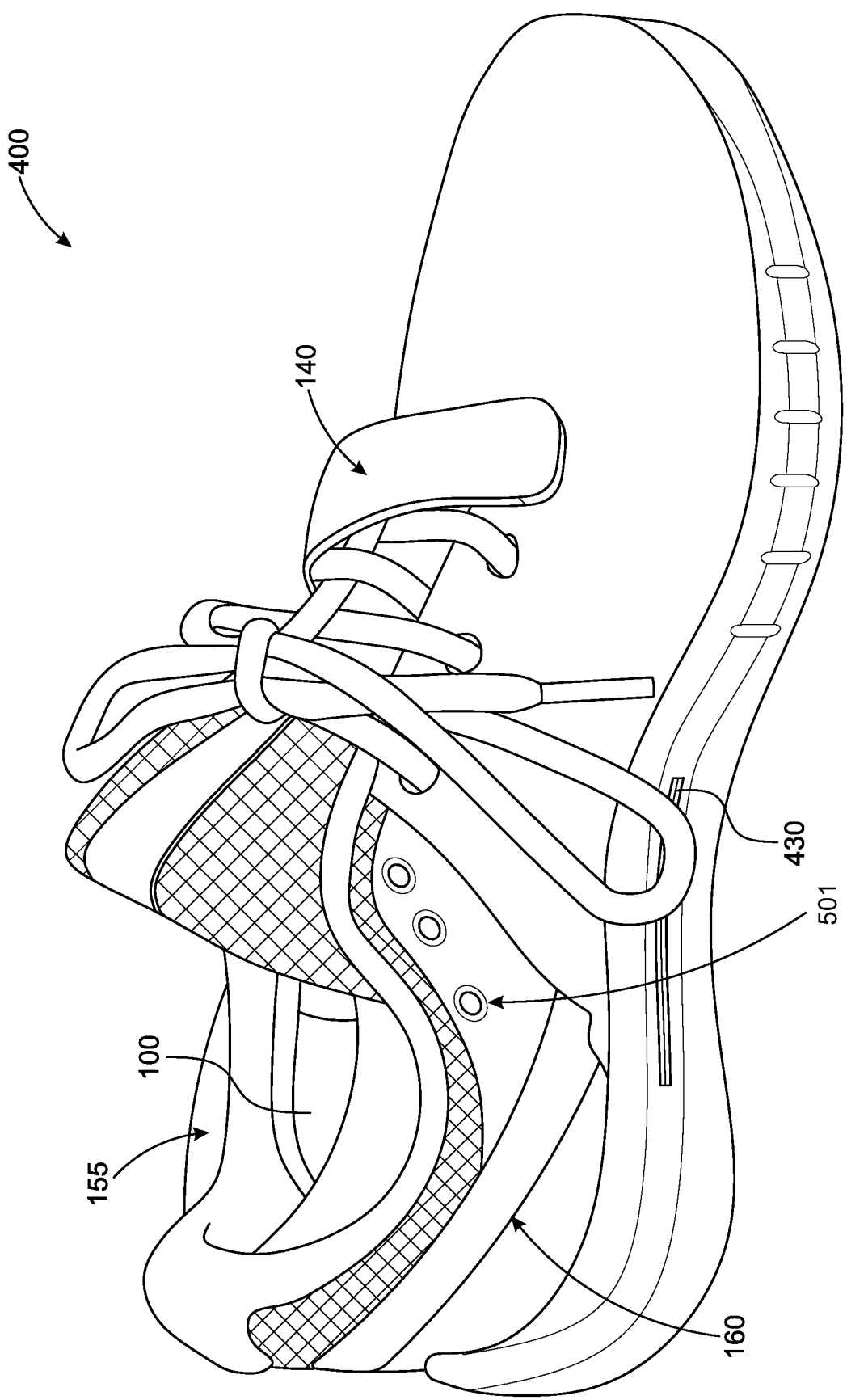
FIG. 5 is a medial elevated view of the left shoe of FIG. 4.
Figure 6:
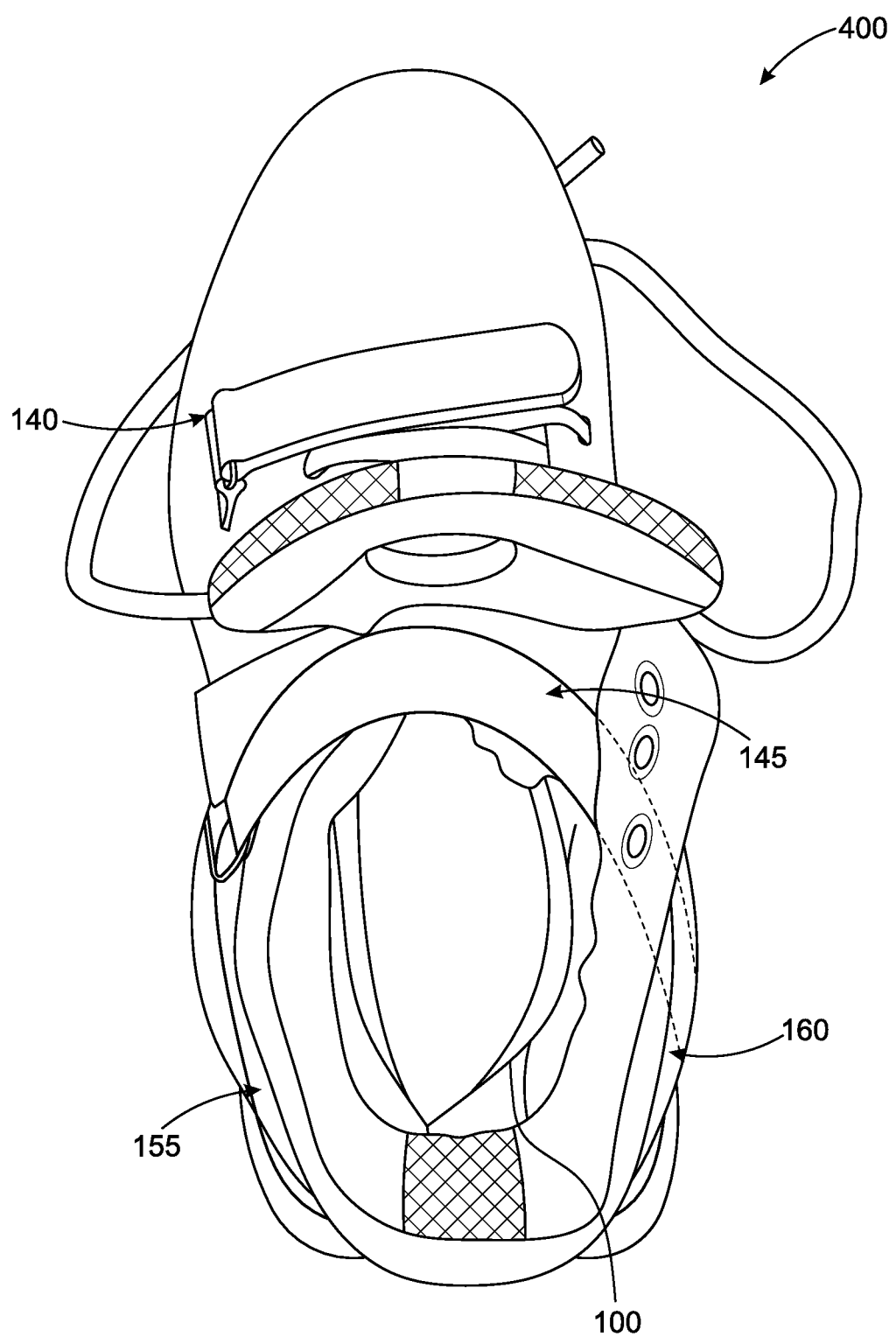
FIG. 6 is a top view of the left shoe of FIG. 4
Figure 7:
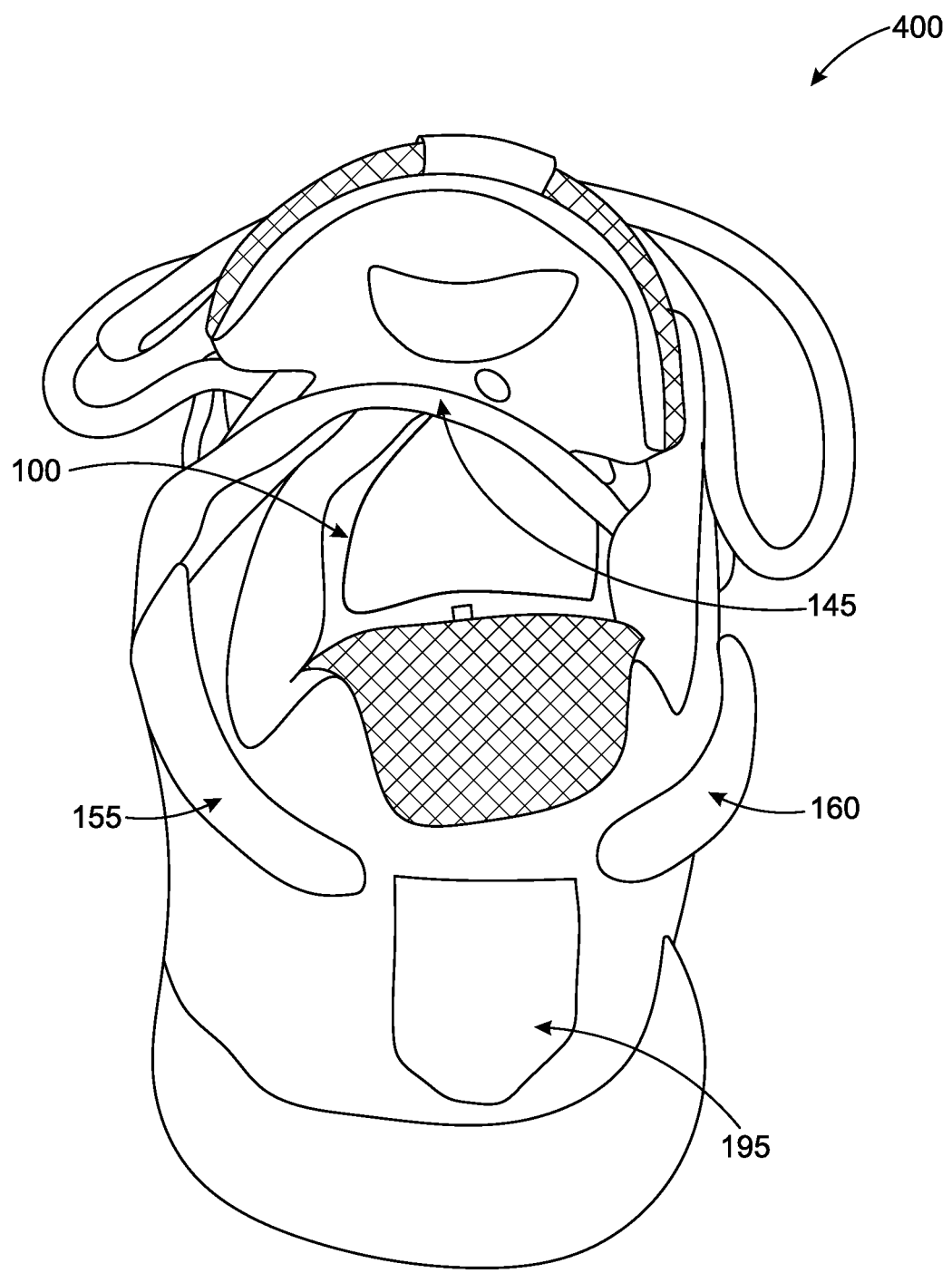
FIG. 7 is a back elevated view of the left shoe of FIG. 4.

FIG. 4 is a lateral elevated view of a left shoe 400, according to one example embodiment. FIG. 5 is a medial elevated view of the left shoe 400. FIG. 6 is a top view of the left shoe 400. FIG. 7 is a back elevated view of the left shoe 400. The adjustable corrective shoe component 100 can be installed in the left shoe 400.

The toe strap 140 may be pulled out over the top of the foot or shoe tongue in the direction of the outside of the medial side of the foot wall over the outside of the shoe and into a d-ring 410 (shown in FIG. 4) attached to the shoe 400 and then can be pulled back to attach on an upper part of the toe strap 140 with a securing yet adjustable type of fastener, such as a hook-and-loop fastener. For example, a VEL-CRO® hook-and-loop fastener or similar can be used. In some other embodiments, the toe strap 140 can be pulled into a loop attached to the shoe 400 or an eyelet integrated in the shoe 400. When pulled up and over the shoe tongue and the foot, the toe strap 140 allows a medial wall of the forefoot section of the shell 110 to conform or correct alignment to a toe area of a foot. The purpose of alignment of the forefoot section of the shell 110 to the foot is to control and or correct the metatarsal heads and toes during foot movements, such as forefoot abduction, inversion, eversion, pronation, and supination. In other embodiments, laces attached to the walls of the forefoot section of the shell 110 can be used. The laces may come through or exit the shoe and can be tightened in many ways, such as such as crisscrossed, folded back onto themselves, or coming through the bottom of the shoe up that is opposite of the sole or shell. The laces can be tightened with a bolt style that can be turned in either direction with a knob, dial, or tool type device.

The navicular strap 145 of the adjustable corrective component 100 may be pulled out over the top of the foot and over or under the shoe tongue in the direction of the outside of the medial side of the foot over the outside of the shoe and into a d-ring 420 attached to lateral side of the shoe. Then navicular strap 145 can be pulled back to attach on the upper part of the navicular strap 145. The attachment can be carried out with a securing yet adjustable type of fastener, such as a hook-and-loop fastener. For example, VELCRO® hook-and-loop fastener or similar can be used. In some other embodiments, the navicular strap 145 can be pulled through a loop attached to the shoe 400 or an eyelet 501 integrated in the shoe 400. The navicular strap 145, when pulled up and over, may allow the inside wall of the mid-section 120 to conform to an arch of a foot. The shell 110 can be made from materials that are semi firm and flexible enough to support and compress against the arch.

In some embodiments, the shell 110 can be made of several layers of materials that allow for semi firm and flexible compressions of a specific arch cut in the shell. The cut may begin at the top of the shell and travel down to the middle of the medial surface or bottom of the shell 110. When the shell 110 touches the foot, the arch cut is located on the medial aspect of the foot, specifically the Sustentaculim Tali area (known in the field of orthotics as a ST dig) that separates the midfoot from the hind foot just beyond the end of the foot arch. When the navicular strap 145 is pulled up and the mid-section 120 conforms to the foot, the arch cut separates and creates a moving floating arch to accommodate any individual's arch height needs. The shell 110 can be made of materials semi firm and flexible enough to support and compress against the arch when pulled in the corrected position.

The outsole of the shoe 400 may have a slit 430. An accessory strap may be added permanently or optionally to figure-8 wrap the ankle and attach to the outer sides of the shoe 400 using a hook and loop fastener, d-ring type loop, or eyelet integrated in the shoe.

The first heel strap 155 attached to the medial side of the hind section of the shell 110 and the second heel strap 160 attached to the lateral side of the hind section of the shell 110 can be crisscrossed within the shoe. The first heel strap 155 can exit out of the shoe heel counter (or back) and be locked at the lateral side of a shoe using, for example, a hook-and-loop fastener. The second heel strap 160 can exit out of the shoe heel counter (or back) and be locked at the medial side of the shoe using, for example, a hook-and-loop fastener. The first heel strap 155 and the second heel strap 160 can be used to compress and secure the hind section of the shell 110 to the heel of the foot. In some other embodiments, the first heel strap 155 and the second heel strap 160 can be locked at the back of the shoe with a cord stop lock. In some embodiments, the shoe 400 may include an inner pocket design 195 of FIG. 7 within the shoe wall or outside of the shoe heel wall to place straps and the cord stop lock.

Figure 8A:
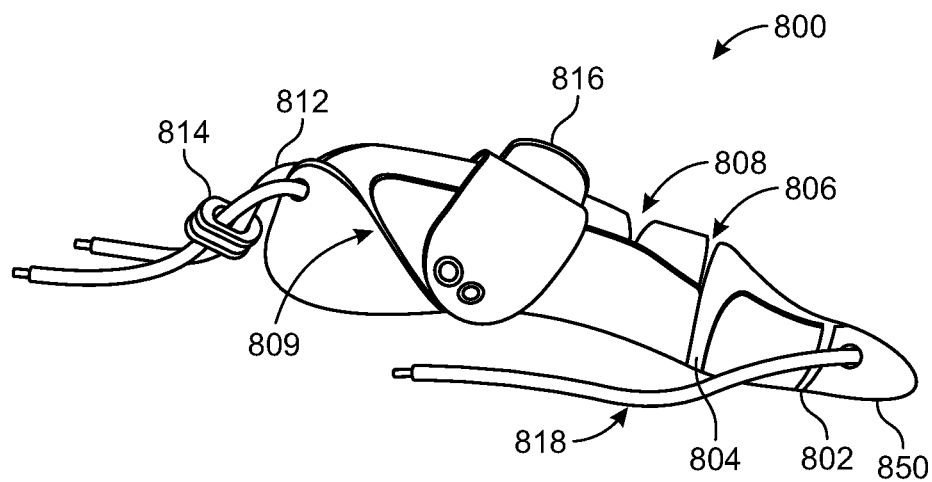
FIG. 8A is a medial view of an adjustable corrective shoe component, according to another example embodiment.
Figure 8B:
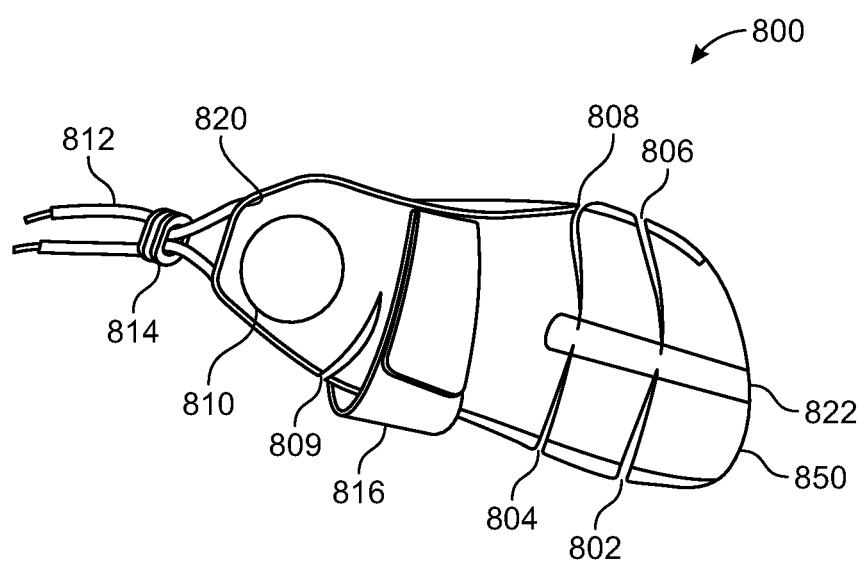
FIG. 8B is a top view of the adjustable corrective shoe component of FIG. 8A.
Figure 8C:
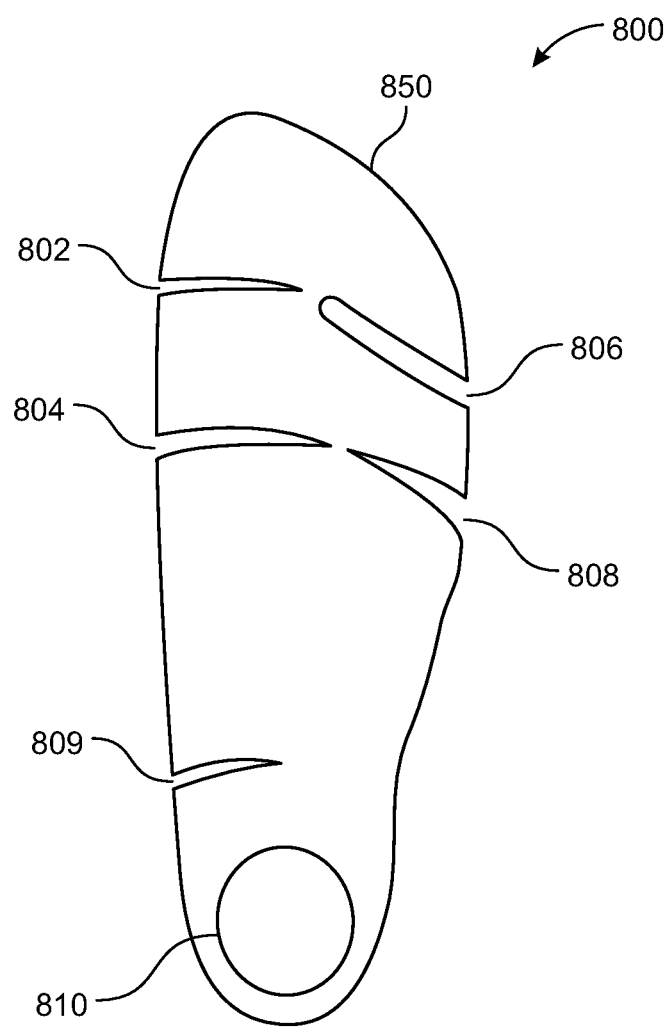
FIG. 8C is a bottom view of the adjustable corrective shoe component of FIG. 8A.

FIG. 8A is a medial view of an adjustable corrective shoe component 800, according to another example embodiment. FIG. 8B is a top view of the adjustable corrective shoe component 800. FIG. 8C is a bottom view of the adjustable corrective shoe component 800. The adjustable corrective shoe component 800 may include a shell 850 made of a semi-rigid material. The shell 850 can be formed conformal to an interior bottom surface of a left shoe and curving upwards at sides of the left shoe. The shell 850 may include a forefoot section, a middle section, and a hind section. In the forefoot section, the shell 850 may include cuts 802, 804, 806, 808, and 809, cutout 810, and base 822. The shell 850 may include an arch cut 809 separating the middle section and the hind section. In the hind section, the shell 850 may include an Achilles "U" cut 820 at a back side of the hind section.

The adjustable corrective shoe component 800 may further include a pull strap 816 attached to a medial side of the middle section. The adjustable corrective shoe component 800 may include crisscross cords 812 attached to both sides of the hind section of the shell 850 and a cord stop 814 to secure the crisscross cords 812. The adjustable corrective shoe component 800 may also include one or more pull cords 818 attached to sides of forefoot sections of the shell 850.

Figure 9A:
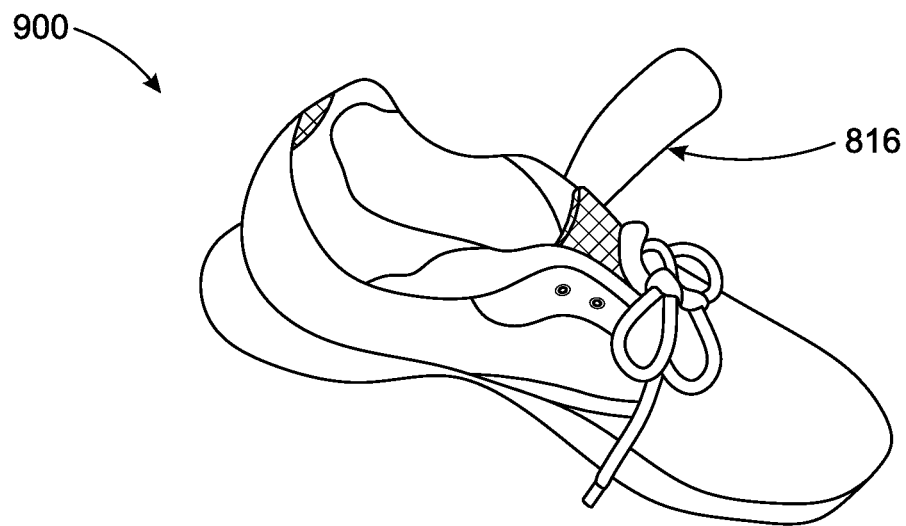
FIG. 9A is medial elevated view of a left shoe 900 with an adjustable corrective shoe component of FIG. 8A, according to an example embodiment.
Figure 9B:
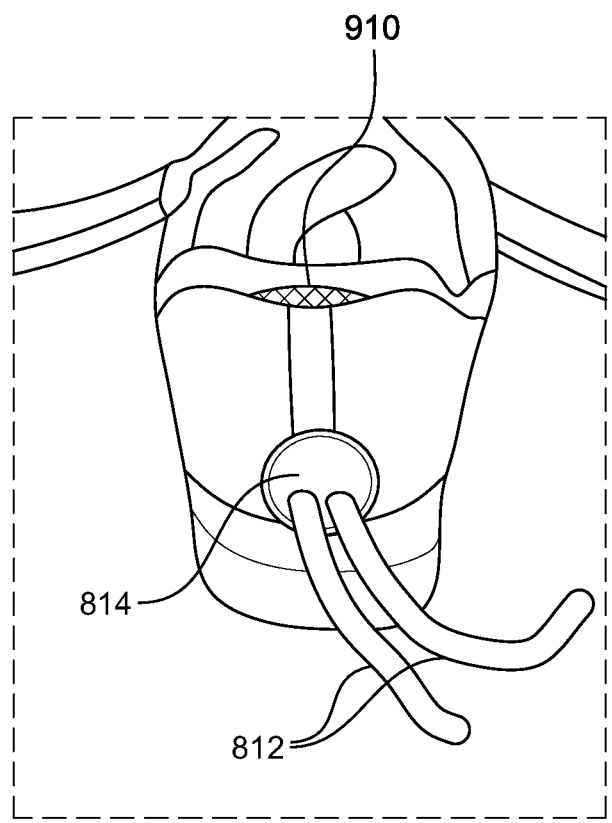
FIG. 9B is a back elevated view of the left shoe of FIG. 9A.
Figure 9C:
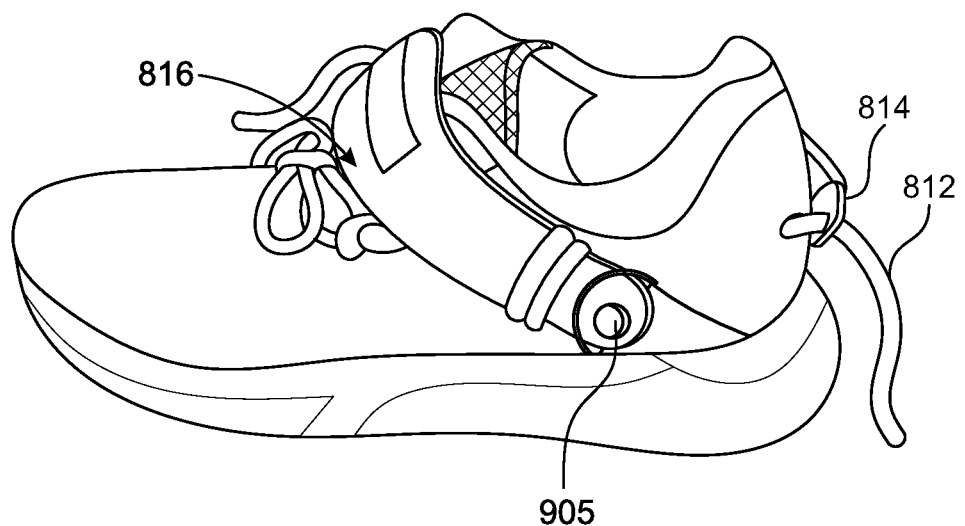
FIG. 9C is a lateral elevated view of the left shoe of FIG. 9A.

FIG. 9A is medial elevated view of a left shoe 900, according to an example embodiment. The adjustable corrective shoe component 800 can be disposed within an inner lining of the left shoe. FIG. 9B is a back elevated view of the left shoe 900. FIG. 9C is a lateral elevated view of the left shoe 900.

The pull strap 816 of the adjustable corrective component 800 can be pulled out over the top of a foot and over or under the shoe tongue in the direction of the outside of medial side of the foot over the outside of the left shoe 900. The pull strap 816 can be pulled through a d-ring 905 attached to lateral side of the left shoe 900. Then the pull strap 816 can be pulled back to attach on the upper part of the pull strap 816 using a hook-and-loop fastener. The shell 850 (shown FIGS. 8B-8C) touches the foot, and the arch cut 809 is located on the medial aspect of the foot at the Sustentaculim Tali area that separates the midfoot from the hind foot just beyond the end of the foot arch. When the pull strap 816 is pulled up, the shell 120 conforms the foot and the arch cut 809 separates and creates a moving floating arch to accommodate any individual's arch height needs. The shell 850 can be made of materials semi firm and flexible enough to support and compress against the arch when pulled in the corrected position.

The cords 812 attached to both sides of the hind section of the shell 850 can be crisscrossed within the left shoe 900. The cords 812 can be further pulled out of the left shoe 900 and secured with a cord stop 814. The ends of the cords 812 can be further disposed in an inner pocket 910 within the back wall of the left shoe 900. When the cords 812 are pulled out the left shoe 900 and secured, the walls of the hind section of the shell 850 conform the heel of the foot. The support of the walls may help to biomechanically control heel eversion and inversion.

Figure 10A:
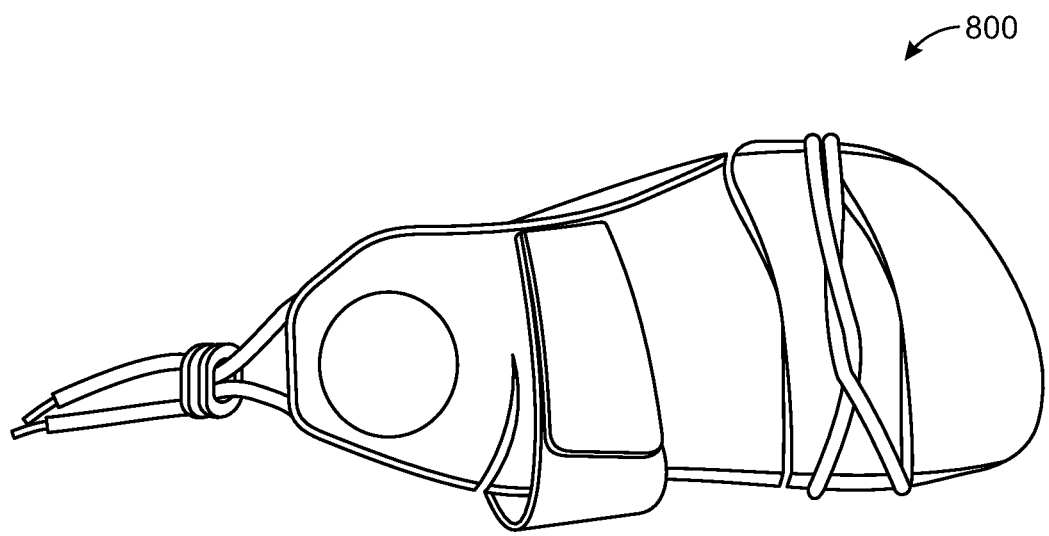
FIG. 10A is a top view of an adjustable corrective shoe component, according to an example embodiment.
Figure 10B:
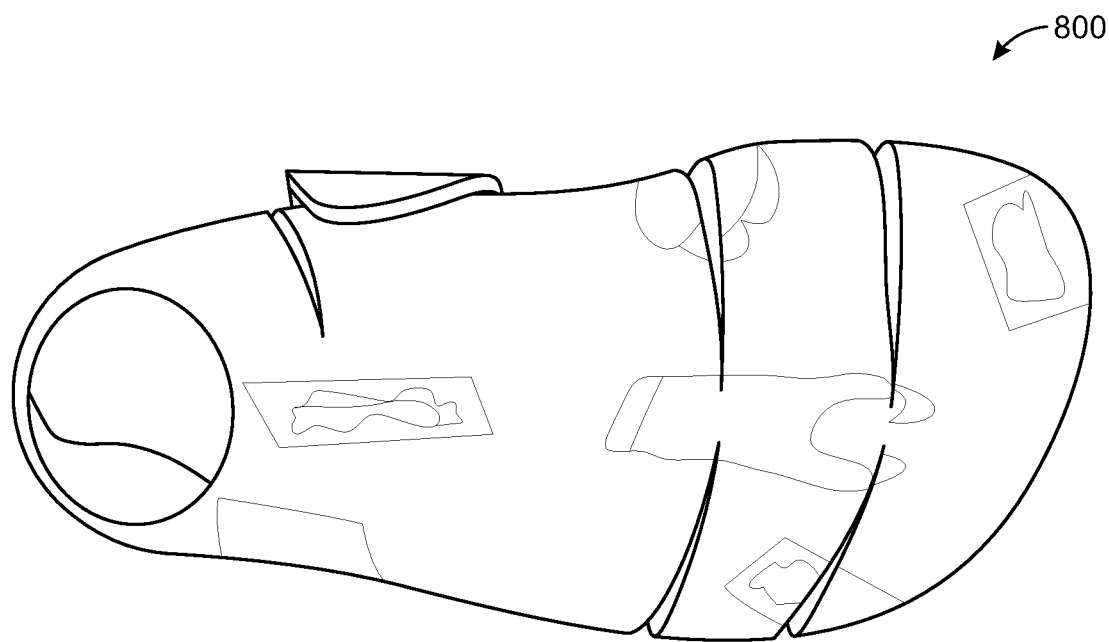
FIG. 10B is bottom view of the adjustable corrective shoe component of FIG. 10A.
Figure 10C:
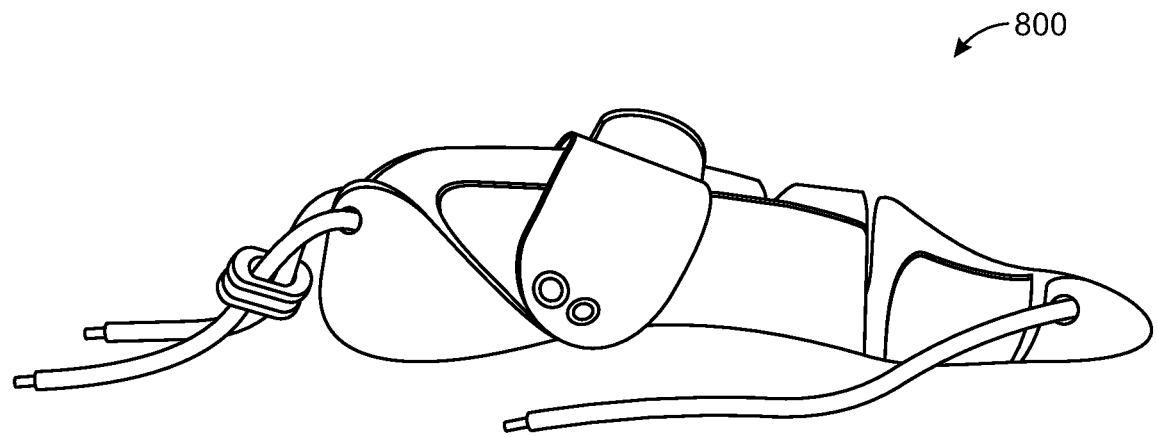
FIG. 10C is medial view of the adjustable corrective shoe component of FIG. 10A.
Figure 10D:
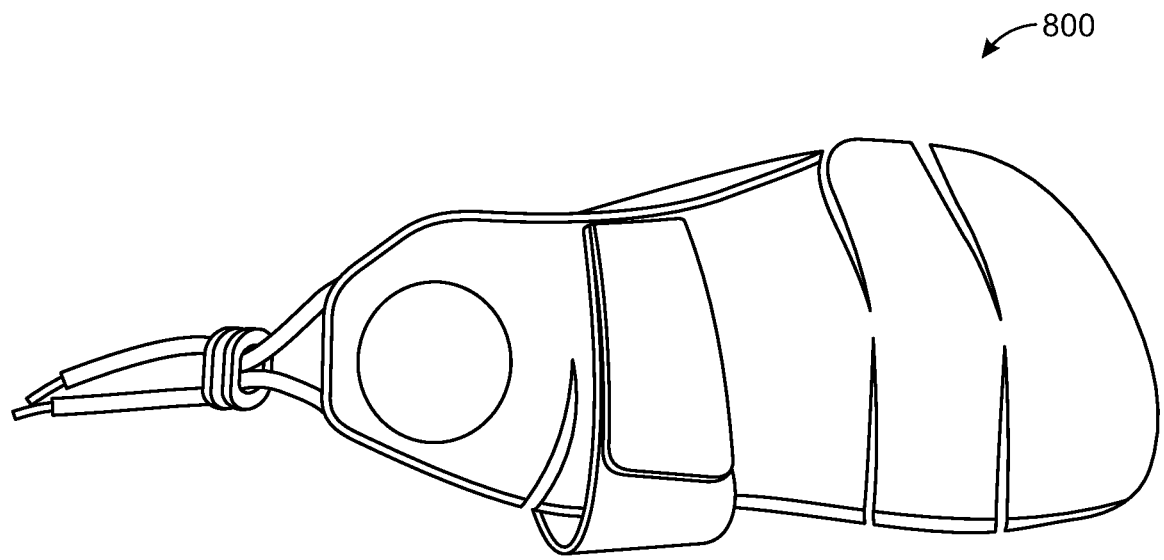
FIG. 10D is a top view of an adjustable corrective shoe component.

FIG. 10A is a top view of an adjustable corrective shoe component 800, according to an example embodiment. FIG. 10B is a bottom view of the adjustable corrective shoe component 800. FIG. 10C is a medial view of the adjustable corrective shoe component 800. FIG. 10D is a top view of the adjustable corrective shoe component 800.

FIG. 11 is a flow chart showing a method 1100 for manufacturing an adjustable corrective show component, according to an example embodiment.

The method 1100 may commence, in block 1102, with providing a shell formed conformal to an interior bottom surface of the shoe and curving upwards at sides of the shoe. The shell may include a forefoot section to accommodate a forefoot area of a foot, a middle section to accommodate a midfoot area of the foot, and a hind section to accommodate a hind area of the foot.

In block 1104, the method 1100 may include providing a strap attached to a medial side of the middle section. The strap can be configured to pull the middle section towards a lateral side of the shoe to cause the middle section to support an arch of the foot.

In block 1106, the method 1100 may include providing a further strap attached to a medial side of the forefoot section. The further strap can be configured to pull the forefoot section towards the lateral side of the shoe to cause the forefoot section to support a metatarsal head or a toe of the foot.

In block 1108, the method 1100 may include providing a first back strap attached to a medial side of the hind section and configured to be pulled through a surface of shoe and towards a lateral external side of the shoe, and so cause the medial side of the hind section to support a medial side of a heel of the foot.

In block 1110, the method 1100 may include providing a second back strap attached to a lateral side of the hind section and configured to be pulled through a surface of shoe and towards a medial external side of the shoe, and so cause the lateral side of the hind section to support a lateral side of the heel of the foot. The first back strap and the second back strap are crisscrossed within the shoe.

Thus, adjustable corrective shoe components are disclosed. While the present embodiments have been described in connection with a series of embodiments, these descriptions are not intended to limit the scope of the subject matter to the particular forms set forth herein. It will be further understood that the methods are not necessarily limited to the discrete components described. To the contrary, the present descriptions are intended to cover such alternatives, modifications, and equivalents as may be included within the spirit and scope of the subject matter as disclosed herein and defined by the appended claims and otherwise appreciated by one of ordinary skill in the art.

What is claimed is:

1. An adjustable corrective shoe component, comprising:
   a shell having a top surface, a bottom surface, a lateral portion that is bent up or bendable upwardly to contact a lateral side of a foot, and a medial portion that is bent up or bendable upwardly to contact a medial side of a foot, wherein the shell comprises:
     a forefoot section to accommodate a forefoot area of a foot placed on the top surface;
     a middle section to accommodate a midfoot area of the foot placed on the top surface; and
     a hind section to accommodate a hind area of the foot placed on the top surface, wherein the hind section includes a "U" cut from a back side of the shell;
   a first strap having a first end secured to the bottom surface of the forefoot section of the shell, extending around the medial portion of the shell, and configured to be wrapped over the forefoot area of the foot placed on the top surface to urge the medial portion of the forefoot section of the shell against the medial side of the foot;
   a second strap having a first end secured to the bottom surface of the middle section of the shell, extending around the medial portion of the shell, and configured to be wrapped over the navicular bone of the foot placed on the top surface to urge the medial portion of the middle section of the shell against the medial side of the foot;
   a third strap secured to the bottom surface of the hind section of the shell, extending around the medial portion of the shell, and configured to be wrapped around the hind area of the foot placed on the top surface to urge the medial portion of the hind section against the medial side of the foot
   a first pillow disposed on the top surface of the medial portion of the shell at the hind section; and
   a second pillow disposed on the top surface of the lateral portion of the shell at the hind section.

2. The adjustable corrective shoe component of claim 1, wherein the shell is made of a flexible material or a semifirm material.

3. The adjustable corrective shoe component of claim 1, wherein the first strap, the second strap, and the third strap are made of a stretch material.

4. A corrective shoe comprising the adjustable corrective shoe component of claim 1, further comprising a shoe in which the shell is installed, and further comprising:
   a first hook-and-loop fastener, wherein the first hook-and-loop fastener is integrated in the first strap;
   a second hook-and-loop fastener, wherein the second hook-and-loop fastener is integrated in the second strap;
   a first eyelet, loop, or d-ring on a lateral side of the shoe; and
   a second eyelet, loop, or d-ring attached to the lateral side of the shoe,
   wherein the first strap is configured to be pulled through the first eyelet, loop, or d-ring attached to the lateral side of the shoe and then pulled back and secured using the first hook-and-loop fastener, and the second strap is configured to be pulled through the second eyelet, loop, or d-ring attached to the lateral side of the shoe and then pulled back and secured using the second hoop-and-loop-fastener.

5. The adjustable corrective shoe component of claim 1, wherein the middle section is separated from the hind section by a notch extending from a medial edge of the shell transversally to a center of the shell.

6. The adjustable corrective shoe component of claim 1, further comprising a fourth strap having a first end secured to the bottom surface of the forefoot section of the shell, extending around the lateral portion of the shell, and configured to be wrapped over the forefoot area of the foot placed on the top surface to urge the lateral portion of the forefoot section of the shell against the lateral side of the foot to cause the forefoot section to support a metatarsal head or a toe of the foot placed on the top surface of the shell.

7. A corrective shoe comprising the adjustable corrective shoe component of claim 6, further comprising a shoe in which the shell is installed, and further comprising:
   a hook-and-loop fastener integrated in the fourth strap; and
   an eyelet, loop, or d-ring on a medial side of the shoe, wherein the fourth strap is configured to be pulled over a surface of the shoe, through the thirds eyelet, loop, or d-ring and then pulled back and secured using a hook-and-loop fastener integrated in the fourth strap.

8. The adjustable corrective shoe component of claim 1, further comprising:
   a lateral hind strap secured to the bottom surface of the hind section of the shell, extending around the lateral portion of the shell, and configured to be wrapped around the hind area of the foot placed on the top surface to urge the lateral portion of the hind section against the lateral side of the foot.

9. The adjustable corrective shoe component of claim 8, further comprising:
   a first hook-and-loop fastener to secure the third strap to itself; and
   a second hook-and-loop fastener to secure the lateral hind strap to itself.

10. The adjustable corrective shoe component of claim 1, wherein the shell comprises a first layer of conformal material and a second layer of a cork material positioned over the first layer, wherein the first layer extends over the forefront section, the middle section, and the hind section, and wherein the second layer extends over the middle section and the hind section.

11. The adjustable corrective shoe component of claim 5, wherein a position of the notch in the shell is centrally located along the medial side of the middle section so that the notch corresponds to the Sustentaculim Tali of the foot.

12. The adjustable corrective shoe component of claim 1, wherein the first end of the second strap is secured to the shell by a first anchor at a middle portion of the middle section and a second anchor positioned on the shell between a medial edge of the shell and the first anchor.

13. The adjustable corrective shoe component of claim 1, wherein the first end of the first strap and the first end of the second strap are positioned centrally towards a longitudinal axis of the shell.

14. The adjustable corrective shoe component of claim 1, wherein a first portion of the third strap extends from a lateral side of the hind section and wherein a second portion of the third strap extends from a medial side of the hind section.

15. A corrective shoe comprising the adjustable corrective shoe component of claim 14, further comprising a shoe in which the shell is installed, wherein the first portion of the third strap is configured to pass through an opening on a medial side of the shoe when the shell is received by the shoe and wherein the second portion of the third strap is configured to pass through an opening on a lateral side of the shoe when the shell is received by the shoe.

* * * * *